(12) United States Patent
Onuki et al.

(10) Patent No.: US 8,298,250 B2
(45) Date of Patent: Oct. 30, 2012

(54) MEDICAL LIGATING APPARATUS

(75) Inventors: Yoshio Onuki, Hino (JP); Satoshi Miyamoto, Nishitama-gun (JP); Koichi Kawashima, Hachioji (JP)

(73) Assignee: Olympus Corporation, Tokyo (JP)

( * ) Notice: Subject to any disclaimer, the term of this patent is extended or adjusted under 35 U.S.C. 154(b) by 930 days.

(21) Appl. No.: 12/324,986

(22) Filed: Nov. 28, 2008

(65) Prior Publication Data

US 2009/0105730 A1 Apr. 23, 2009

Related U.S. Application Data

(63) Continuation of application No. 11/643,581, filed on Dec. 21, 2006, which is a continuation of application No. 10/341,762, filed on Jan. 14, 2003, now abandoned.

(30) Foreign Application Priority Data

Jan. 16, 2002 (JP) .................................. 2002-007687

(51) Int. Cl.
*A61B 17/24* (2006.01)
*A61B 17/10* (2006.01)
*A61B 17/04* (2006.01)

(52) U.S. Cl. .................... 606/148; 606/113; 606/139
(58) Field of Classification Search ................. 606/139, 606/144, 170, 113, 148, 110, 138
See application file for complete search history.

(56) References Cited

U.S. PATENT DOCUMENTS

| 5,242,459 A | 9/1993 | Buelna |
|---|---|---|
| 5,417,702 A | 5/1995 | Hempel |
| 5,810,845 A | 9/1998 | Yoon |
| 5,855,586 A | 1/1999 | Habara et al. |
| 5,908,429 A | 6/1999 | Yoon |
| 2003/0167062 A1* | 9/2003 | Gambale et al. .............. 606/138 |

FOREIGN PATENT DOCUMENTS

| JP | 48-71090 | 9/1973 |
|---|---|---|
| JP | 54-30692 | 3/1979 |
| JP | 8-98840 | 4/1996 |
| JP | 10-194 | 1/1998 |
| JP | 10-277046 | 10/1998 |
| JP | 11-244294 | 9/1999 |
| JP | 11-511362 | 10/1999 |
| JP | 2001-502190 | 2/2001 |
| WO | WO 97/09935 | 3/1997 |
| WO | WO 97/30639 | 8/1997 |

OTHER PUBLICATIONS

Japanese Office Action dated Mar. 23, 2010 with translation.
Two (2) Japanese Office Actions dated Oct. 20, 2009 with translations.

* cited by examiner

*Primary Examiner* — Corrine M McDermott
*Assistant Examiner* — Melissa Ryckman
(74) *Attorney, Agent, or Firm* — Scully, Scott, Murphy & Presser, P.C.

(57) ABSTRACT

A medical ligating apparatus includes a medical ligating device having a member which is made of a flexible line and ligates living tissues, and a fixing member which is movably provided at the ligating member and fixes the living tissues in a ligated state, a manipulating device having a flexible sheath and a proximal manipulating section, and a cutting member for cutting the ligating member. The cutting member is provided on the manipulating device and is movably provided on the ligating member.

10 Claims, 7 Drawing Sheets

MEDICAL LIGATING APPARATUS

CROSS-REFERENCE TO RELATED APPLICATIONS

This application is a continuation application of U.S. Ser. No. 11/643,581, filed Dec. 21, 2006 which is a continuation of U.S. Ser. No. 10/341,762, filed Jan. 14, 2003, now abandoned, which is based upon and claims the benefit of priority from the prior Japanese Patent Application No. 2002-7687, filed Jan. 16, 2002, the entire contents of each of which are incorporated herein by reference.

BACKGROUND OF THE INVENTION

1. Field of the Invention

The present invention relates to a medical ligating apparatus for ligating living tissues by inserting the apparatus into a body in a trans-endoscopic manner.

2. Description of the Related Art

Conventionally, medical ligating apparatuses for ligating a lesion of a living tissue, such as polyp, by inserting the apparatuses through endoscope channels, and inserting them into cavities in a trans-endoscopic manner are known from Jpn. Pat. Appln. KOKAI Publication Nos. 10-194, 10-277046, 11-244294, 48-71090, 8-98840, and 54-30692 and the like. These medical ligating apparatuses are composed of: a sheath that can be inserted through an endoscope channel; a manipulating wire movably inserted through this sheath; a loop shaped ligating wire removably connected to a distal end of this manipulating wire; and a stopper provided at a proximal end of this ligating wire.

In this medical ligating apparatus, when a ligating wire is hooked on a lesion of a living tissue, such as polyp and a manipulating wire is pulled toward a proximal manipulating section side, a stopper moves relatively to the distal end side of the ligating wire. As a result, the loop of the ligating wire is reduced in diameter. Then, the lesion is tightly bound. A blood flow at the lesion is stopped by this ligation, and thus, the lesion tissue necroses and slips off several days later in a ligated state. Then, a ligating device consisting of the ligating wire and the stopper slips off at the same time, and is naturally discharged from the anus.

The ligating wire is formed of, for example, a synthetic resin such as nylon or polyolefin, or alternatively, stainless steel. The stopper is formed of a thin tube consisting of an elastic element such as silicon rubber. In addition, the stopper is a knot formed at a part of the ligating wire as disclosed in Jpn. Pat. Appln. KOKAI Publication No. 48-71090.

After the ligating wire has been tightly bound on the lesion, it is required to isolate the ligating wire and manipulating wire connected to each other. Therefore, as disclosed in Jpn. Pat. Appln. KOKAI Publication No. 48-71090, a scissors is inserted through the endoscope channel, and a proximal end of the ligating wire is cut by the scissors. As disclosed in Jpn. Pat. Appln. KOKAI Publication No. 54-30692, a cutter member is provided at the distal end of a sheath, and a ligating wire is cut by the cutter member.

However, as described previously, after the ligating wire has been tightly bound on the lesion, the scissors is inserted through the endoscope channel in order to isolate the ligating wire and manipulating wire connected with each other. In a manipulation for cutting the proximal end of the ligating wire by the scissors, it is required to replace the medical ligating device with the scissors, and insert it into a body cavity in a trans-endoscopic manner. Thus, there is a problem that an operation time is extended.

In addition, with a structure in which an openable cutter member is provided in the distal end of the sheath as shown in FIG. 7 of Jpn. Pat. Appln. KOKAI Publication No. 54-30692, a large number of parts are required, resulting in higher manufacturing cost. In addition to wires of the ligating device, the manipulating wire for actuating the cutter member is inserted into the sheath. Thus, the sheath is increased in diameter, making it difficult to insert the sheath into an endoscope having a channel with its small internal diameter.

In the case of the cutter member in which a blade oriented in the transverse direction at a proximal end side as shown in FIG. 8 of Jpn. Pat. Appln. KOKAI Publication No. 54-30692 is provided in a cylindrically shaped member, there is a problem that its manufacture is very difficult, and the sheath is increased in diameter.

Further, in the conventional medical ligating apparatuses, the proximal end of the ligating wire is cut, thereby isolating the ligating wire and manipulating wire connected with each other. Thus, the ligating wire remains in the body cavity while this wire is extended from a ligating section. Therefore, for example, interference with another treatment device or endoscope may occur.

BRIEF SUMMARY OF THE INVENTION

It is an object of the present invention to provide a medical ligating apparatus in which a fixing member for fixing living tissues while they are ligated by a ligating member is provided, ligation is carried out by the ligating member, and then, the ligating member can be cut at a proximal end of the fixing member by a series of manipulations.

According to the present invention, there is provided a medical ligating apparatus comprising: a medical ligating device consisting of a ligating member which consists of a flexible wire rod and ligates living tissues, and a fixing member which is movably provided at the ligating member and fixes the living tissues in a ligated state; and a manipulating device having a flexible sheath and a proximal manipulating section, wherein the manipulating device comprises cutting means for cutting the ligating member, the cutting means movably provided on the ligating member and can move back and forth.

According to the present invention, in the medical ligating apparatus, the manipulating device comprises cutting means for cutting the ligating member, the cutting means being movably provided on the ligating member, and the cutting means is advanced and retracted or rotated so that the ligating member can be cut at a proximal end of the fixing member.

Further, according to the present invention, in the medical ligating apparatus, the manipulating device comprises cutting means for cutting the ligating member, the cutting means being movably provided on the ligating member, and the medical ligating device comprises a receiving member for receiving the cutting means, the receiving member being movably provided on the ligating member.

According to the invention, there is provided a medical ligating device, a ligating member which includes a flexible wire rod and ligates living tissues; a fixing member which is movably provided on the ligating member that fixes the living tissues in a ligated state; and cutting means for cutting the ligating member, the cutting means being provided on the fixing member.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiment of the invention, and together with the general description given above and the detailed description of the preferred embodiment given below, serve to explain the principles of the invention.

DETAILED DESCRIPTION OF THE INVENTION

Hereinafter, embodiments of the present invention will be described with reference to the accompanying drawings.

Figure 1:
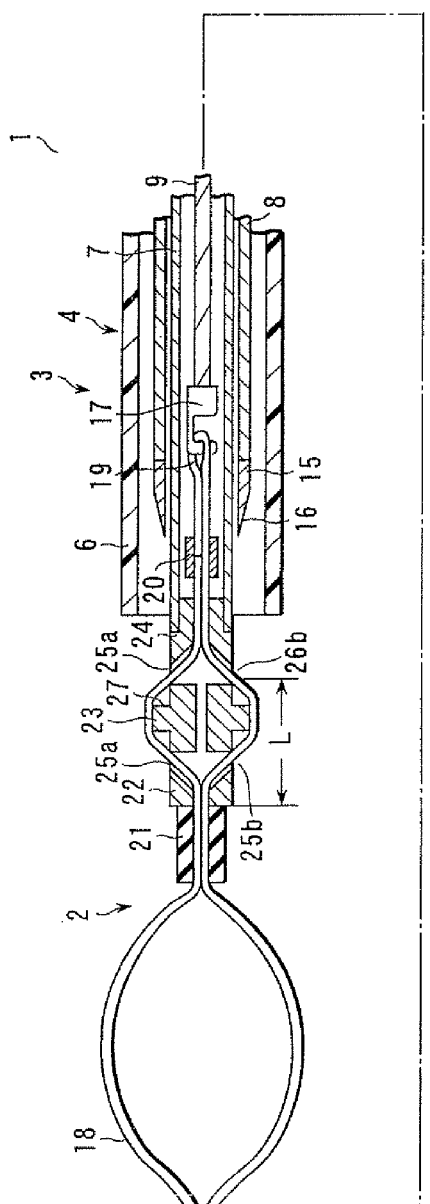
FIG. 1 is a structural view showing an entire medical ligating apparatus according to a first embodiment of the present invention, in which its distal end is cross-sectioned.
Figure 1:
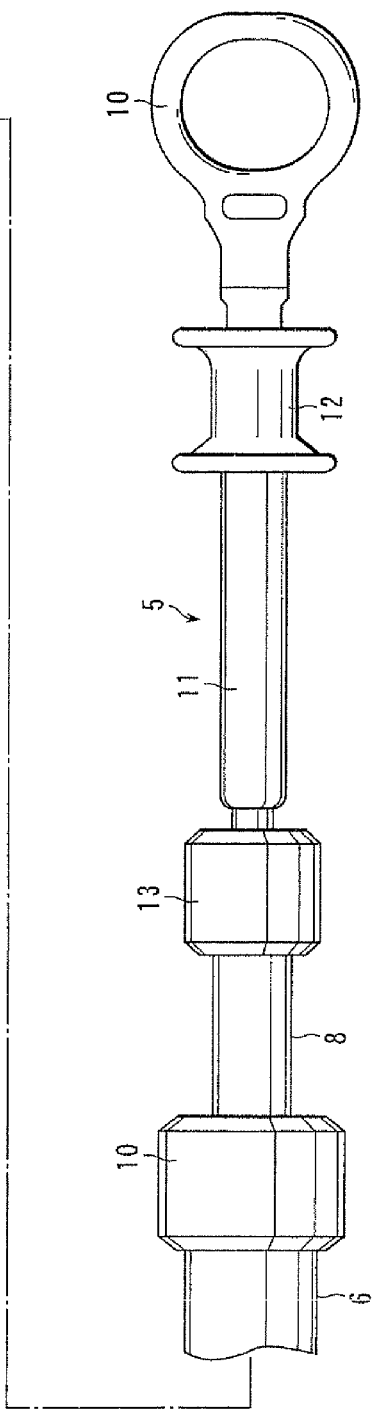
Figure 2:
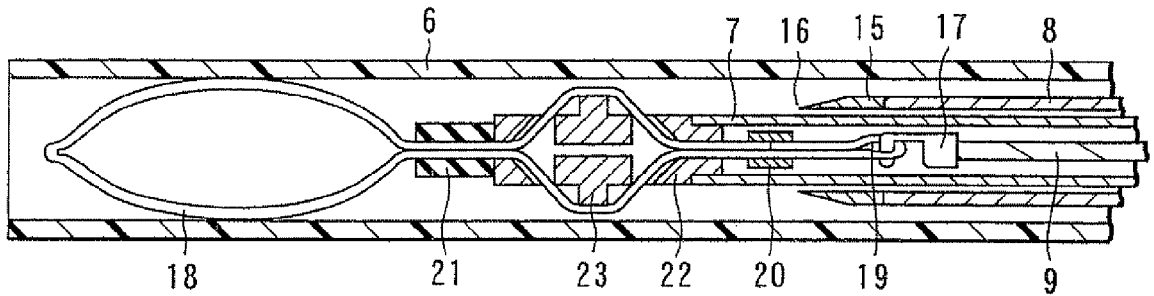
FIG. 2 is a longitudinal side cross section showing a distal end of the medical ligating apparatus according to the first embodiment.
Figure 3:
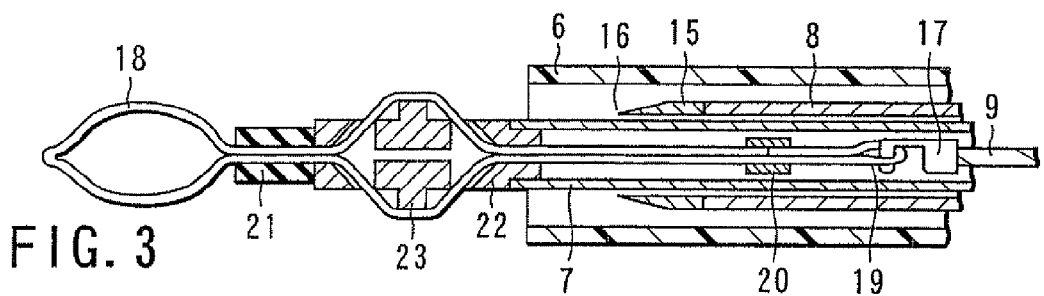
FIG. 3 is a longitudinal side cross section showing a distal end of the medical ligating apparatus according to the same embodiment.
Figure 4:
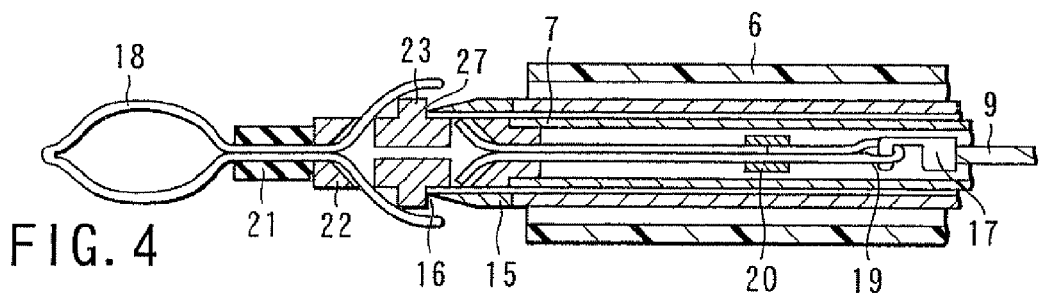
FIG. 4 is a longitudinal side cross section showing a distal end of the medical ligating apparatus according to the first embodiment.
Figure 5:
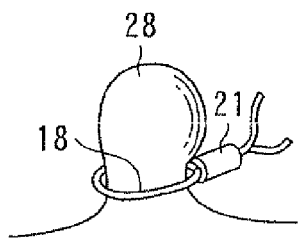
FIG. 5 is a perspective view showing a state in which a lesion is ligated by a ligating wire according to the first embodiment.

FIG. 1 to FIG. 5 show a first embodiment of the present invention. FIG. 1 is a structural view showing an entire medical ligating apparatus, in which its distal end is cross-sectioned. FIG. 2 to FIG. 4 are longitudinal side cross sections of the distal end. FIG. 5 is a perspective view showing a state in which a lesion is ligated by a ligating wire.

As shown in FIG. 1, a medical ligating apparatus 1 is composed of: a medical ligating device 2 retained in a living body; and a manipulating device 3 for guiding the medical ligating device 2 into the living body, thereby carrying out ligating manipulation. The manipulating device 3 is composed of: an insert section 4 having flexibility, the insert section being inserted into an endoscope channel; and a proximal manipulating section 5.

The insert section 4 is composed of: an outer sheath 6 that consists of a flexible sheath; an inner sheath 7 that consists of a flexible sheath and is movably inserted into the outer sheath 6 in an axial direction; a cutting sheath 8 engaged with the outer of the inner sheath 7, the cutting sheath being movably inserted in an axial direction; and a manipulating wire 9 that is retractable in an axial direction, the manipulating wire being inserted through the inner sheath 7.

The outer sheath 6 is made of, for example, a plastic having flexibility such as polyethylene or PTFE, and is 2 mm to 5 mm in diameter. In addition, the inner sheath 7 is made of, for example, a plastic having flexibility such as polyethylene or PTFE. A metallic-meshed sheath may be inserted in a plastic sheath. The manipulating wire 9 is formed of a metal twist wire such as stainless steel.

The proximal manipulating section 5 is composed of: a grip 10 fixed to a proximal end of the outer sheath 6; a slider 12 fixed to a proximal end of the manipulating wire 9, the slider being retractable relative to a manipulating section main body 11; a cutting manipulating section 13 fixed to a proximal end of the cutting sheath 8; and a finger hook ring 14. The outer sheath 6, manipulating wire 9, and cutting sheath 8 can be moved relatively in the forward and backward direction by means of the grip 10, slider 12, and cutting manipulating section 13.

At a distal end of the cutting sheath 8, there is provided an annular cutting member 15 made of a metal such as stainless steel, the cutting member serving as cutting means. A sharp cutting blade 16 is provided all around the distal end of the cutting member 15. In addition, a hook shaped engagement member 17 is securely fixed to the distal end of the manipulating wire 9.

Next, a description of the medical ligating device 2 will be given. In the medical ligating device 2, there is provided a loop shaped ligating wire 18 serving as a ligating member for ligating living tissues at the distal end portion of the device. The ligating wire 18 is formed of a synthetic resin such as nylon or polyolefin, a metal thin wire such as stainless, a silk yarn, or biologically absorptive yarn, and is 0.2 mm to 1 mm in wire diameter. The ligating wire 18 may be in any form of a single wire, twist wire, or knitted wire. In addition, the proximal end side of the ligating wire 18 is folded, and a fold section 19 is formed. Both ends of the ligating wire 18 and the parallel two wires are fixed to an internal cavity of a connecting pipe 20 serving as a fixing parts by means of adhesive bonding or the like.

At the intermediate portion of the ligating wire 18, a tubular stopper 21 serving as a fixing member that is retractable on the wire is movably engaged. The stopper 21 is made of, for example, a rubber such as silicon rubber or fluorine rubber or a variety of thermoplastic elastomers, or a knot of the ligating wire 18. The stopper 21 is advanced, whereby a loop section is reduced in diameter. The stopper 21 is retracted, whereby the loop section is increased in diameter.

A receiving member 22 for receiving the cutting member 15 is provided at the ligating wire 18 at the proximal end of the stopper 21. The receiving member 22 is formed in a cylindrical shape, and is formed of a metal such as stainless or a plastic such as polypropylene, ABS, polyacetal, polycarbonate or the like. An annular protrusion 23 is integrally provided at a substantially intermediate portion in an axial direction. A converging section 24 is provided at the proximal end of the receiving member 22. The converging section 24 is designed so as to be supported after being inserted into the distal end of the inner sheath 7. Therefore, there is no step between an outer periphery face of the inner sheath 7 and an outer periphery face of the receiving member 22 so that the cutting sheath 8 can be advanced and retracted smoothly.

A pair of distal end holes 25a, 25b through which the ligating wire 18 can be inserted are punched at the distal end side more than the annular protrusion 23 of the receiving member 22. A pair of proximal end holes 26a, 26b through which the ligating wire 18 can be inserted are punched at the proximal end side more than the annular protrusion 23. The inner face at the distal end side of the distal end holes 25a, 25b and the inner face at the proximal end side of the proximal end holes 26a, 26b are formed on an incline face so that the ligating wire 18 can be easily inserted and withdrawn. Further, a side face at the proximal end side of the annular protrusion 23 is formed as an abutment face 27 of the cutting member 15.

Each of the folded portions of the ligating wire 18 is led from a proximal opening of the receiving member 22 to the inner of the receiving member 22. Next, these portions each are led from the proximal end holes 26a, 26b to the outer of the receiving member 22. Then, these portions each are led from the distal end holes 25a, 25b to the inner of the receiving member 22 via the outer of the annular protrusion 23. Finally, these portions each are led from the distal opening to the outer. At the distal end side of the receiving member 22, the ligating wire 18 is pressed into an internal cavity of the stopper 21 in a bound state. Further, the full length of the receiving member 22 is about 5 mm to 10 mm. The length of the remaining wire after cut is determined depending on a dimension L between its distal face of receiving member 22 and proximal end holes 26a, 26b each. Thus, the shorter L is desirable, and is set to about 2 mm to 5 mm.

Figure 15:
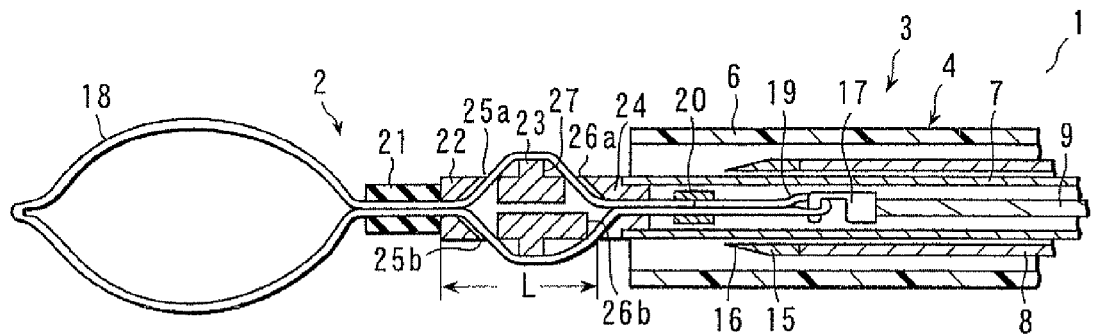
FIG. 15 is a longitudinal side cross section showing a distal end of a medical ligating apparatus showing a modified example of the first embodiment of the present invention.

Now, dimensions of the receiving member 22, annular protrusion 23, and cutting member 15 will be described here. Assume that an external diameter of the receiving member 22 is A, an external diameter of the annular protrusion 23 is B, and an internal diameter of the cutting member 15 is C. These diameters are about 1 mm to 3 mm, and a relationship of A<C, B>C, and B−A=about 0.2 mm to 1 mm is established. In addition, the proximal end holes 26a, 26b, as shown in FIG. 15, may be spaced forwardly or backwardly, respectively.

Now, an operation of the first embodiment will be described here.

First, the slider 12 is manipulated, whereby the manipulating wire 9 is advanced, and the engagement member 17 is protruded from distal openings of the outer sheath 6 and inner sheath 7. In this state, the fold section 19 at the proximal end of the ligating wire 18 is hooked on a hook section of the engagement member 17. When the slider 12 is manipulated, thereby retracting the manipulating wire 9 and introducing the engagement member 17 into the inner of the inner sheath 7, the converging section 24 of the receiving member 22 is supported after being inserted into the distal opening of the inner sheath 7. In this state, when the grip 10 is manipulated, thereby advancing the outer sheath 6, the ligating wire 18 is housed into the inner of the outer sheath 6, and a loop section is reduced in diameter, as shown in FIG. 2.

In this state, the insert section 4 is inserted through the endoscope channel, and is inserted into a body cavity. Then, a distal end of the insert section 4 is guided to a target site in the body cavity. While a lesion 28 such as polyp is observed by means of an endoscope, when the grip 10 is manipulated, thereby retracting the outer sheath 6, the ligating wire 18 is protruded from the distal opening of the outer sheath 6. Then, the loop section of the ligating wire 18 is elastically restored, and is increased in diameter, as shown in FIG. 1.

Next, while the lesion 28 is observed by means of the endoscope, after the loop section of the ligating wire 18 has been hooked on a root of the lesion 28, the slider 12 is manipulated, thereby retracting the manipulating wire 9. Then, the proximal end of the ligating wire 18 is introduced into the inner of the inner sheath 7 via the engagement member 17, and the stopper 21 and receiving member 22 move in a distal end direction of the ligating wire 18. Therefore, the loop section of the ligating wire 18 is reduced in diameter, as shown in FIG. 3, and the lesion 28 is tightly bound. The blood flow to the lesion 28 is stopped by this ligation.

Next, while the slider 12 is held, when the cutting manipulating section 13 is manipulated, thereby advancing the cutting sheath 8, the cutting sheath 8 is advanced while it is guided to the inner sheath 7. Then, the cutting member 15 is engaged with the proximal end of the receiving member 22, and the cutting blade 16 abuts against the abutment face 27. Therefore, the proximal end side of the ligating wire 18 inserted into the receiving member 22 is cut in the vicinity of the proximal end holes 26a, 26b, as shown in FIG. 4.

At this time, the proximal end side of the ligating wire 18 is pulled by the manipulating wire 9, and a tensile stress is applied. Thus, the cutting blade 16 cuts well. In FIG. 4, a time difference may occur without the two top and bottom ligating wires 18 being cut at the same time. However, the two top and bottom ligating wires 18 are connected to each other by means of the connecting pipe 20. Even if these wires are cut one by one, a tensile stress is maintained, and thus, the cutting performance is not degraded.

In the case where the proximal end holes 26a, 26b are displaced forwardly and backwardly, after one of the ligating wires 18 has been cut by the cutting blade 16, the other ligating wire 18 is cut. As a result, both of the ligating wires 18 and the cutting blade 16 do not come into contact with each other at the same time. Thus, the cutting force applied to the ligating wire 18 is not dispersed, and the cutting is made easy.

When the proximal end side of the ligating wire 18 is cut, the inner sheath 7 and receiving member 22 are separated from each other. Then, the ligating device 2 and manipulating device 3 are completely separated from each other. When the insert section 4 is drawn from the endoscope channel, the receiving member 22 slips off from the cut proximal end of the ligating wire 18. Therefore, as shown in FIG. 5, only the ligating wire 18 held in a tightly bound state by means of the stopper 21 is retained in the body, and a surgical operation for tightly binding the lesion 28 completes. The receiving member 22 having slipped off from the ligating wire 18 is naturally discharged to the outer of the body via the digestive tract.

In this way, according to the medical ligating apparatus 1, a manipulation for tightly binding the lesion 28 by the ligating wires 18 and a manipulation of cutting and separating the ligating wires 18 can be carried out in series. Therefore, unlike the prior art, there is no need to replace the ligating apparatus with the scissors in the endoscope channel, and a surgical operation time can be reduced. Moreover, the ligating wire 18 can be cut at a portion close to the stopper 21. Thus, the ligating wire 18 does not remain in the body cavity while being in an expanded state, and interference with another treatment device or an endoscope can be prevented.

Such a simple structure is provided that the cutting means 15 having the cutting blade 16 oriented in the longitudinal direction of the manipulating device 3 is mounted at the distal end of the cutting sheath 8, thus making it possible to reduce the manufacturing cost of the manipulating device and reduce the manipulating device in diameter. Further, even when the cutting performance of the cutting blade 16 is degraded due to repeated use of the manipulating device 3, the cutting sheath 8 and cutting means 15 can be easily replaced by removing them from the manipulating device 3.

Figure 6:
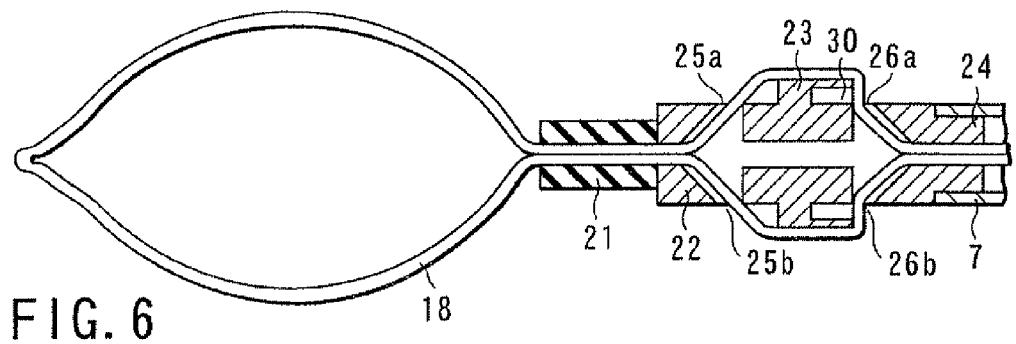
FIG. 6 is a longitudinal side cross section showing a distal end of a medical ligating apparatus according to a second embodiment of the present invention.
Figure 7:
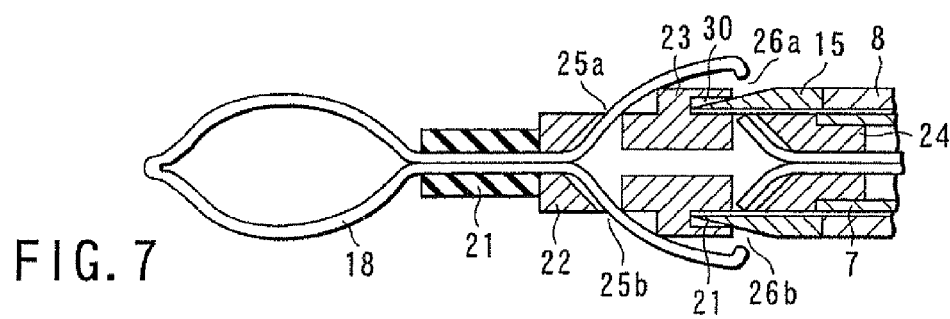
FIG. 7 shows the second embodiment and is a longitudinal, side cross-sectional view of the distal end of the medical ligating apparatus.

FIG. 6 and FIG. 7 show a second embodiment of the present invention. Like elements in the first embodiment are designated by like reference numerals. A duplicate description is omitted here. FIG. 6 and FIG. 7 are longitudinal side cross sections showing a distal end side of a medical ligating apparatus. An annular groove 30 into which the cutting blade 16 of the cutting member 15 is to be inserted is provided on the proximal side face of the annular protrusion 23 of the receiving member 22 according to the present embodiment.

Therefore, while the slider 12 is maintained, when the cutting manipulating section 13 is manipulated, thereby advancing the cutting sheath 8, the cutting sheath 8 is advanced while it is guided to the inner sheath 7. Then, the cutting blade 16 of the cutting member 15 is inserted into the annular groove 30 of the receiving member 22. Therefore, the proximal end side of the ligating wire 18 inserted into the receiving member 22 is cut in the vicinity of the proximal end holes 26a, 26b, as shown in FIG. 7. At this time, the cutting blade 16 is guided to the annular groove 30, whereby the blade does not slip on the wire, and can cut the wire reliably. In addition, the cutting performance is improved more significantly.

Figure 8:
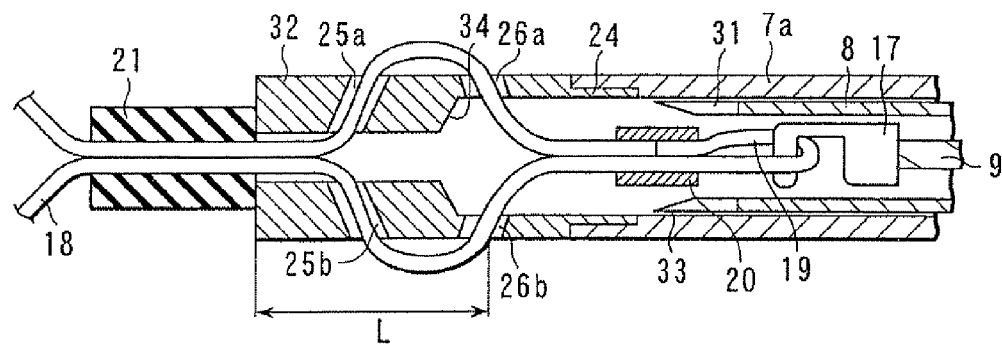
FIG. 8 shows a third embodiment and is a longitudinal, side cross-sectional view of the distal end of the medical ligating apparatus.

FIG. 8 shows a third embodiment of the present invention. Like elements in the first embodiment are designated by like reference numerals. A duplicate description is omitted here. FIG. 8 is a longitudinal side cross section showing a distal end side of a medical ligating apparatus. The cutting member 31 of the present embodiment is provided at the inner of a sheath 7a so as to be advanced and retracted by means of the cutting sheath 8. The cutting member 31 may be removable from the cutting sheath 8 so as to facilitate replacement.

In addition, a receiving member 32 is formed in a cylindrical shape that does not have an annular protrusion, and the distal end holes 25a, 25b and the proximal end holes 26a, 26b are provided. An abutment face 34 of a cutting blade 33 of a cutting member 31 is provided on an internal wall of the receiving member 32.

Therefore, when the cutting manipulating section 13 is manipulated, thereby advancing the cutting sheath 8, the cutting sheath 8 is advanced while it is guided to the sheath 7a. Then, the cutting blade 33 of the cutting member 31 abuts against the abutment face 34 of the receiving member 32. Therefore, the proximal end side of the ligating wire 18 inserted into the receiving member 32 is cut in the vicinity of the proximal end holes 26a, 26b.

As in the present embodiment, the cutting member 31 is provided at the inner of the sheath 7a, whereby any protrusion is eliminated at the outer of the sheath 7a, and the cutting blade is not exposed. In this way, the outer sheath is eliminated, and thus, wiring can be directly provided to the endoscope channel. The outer sheath is eliminated, whereby the insert section 4 of the medical ligating apparatus 1 is reduced in diameter, and wiring can be provided to a channel with its small internal diameter.

Figure 9:
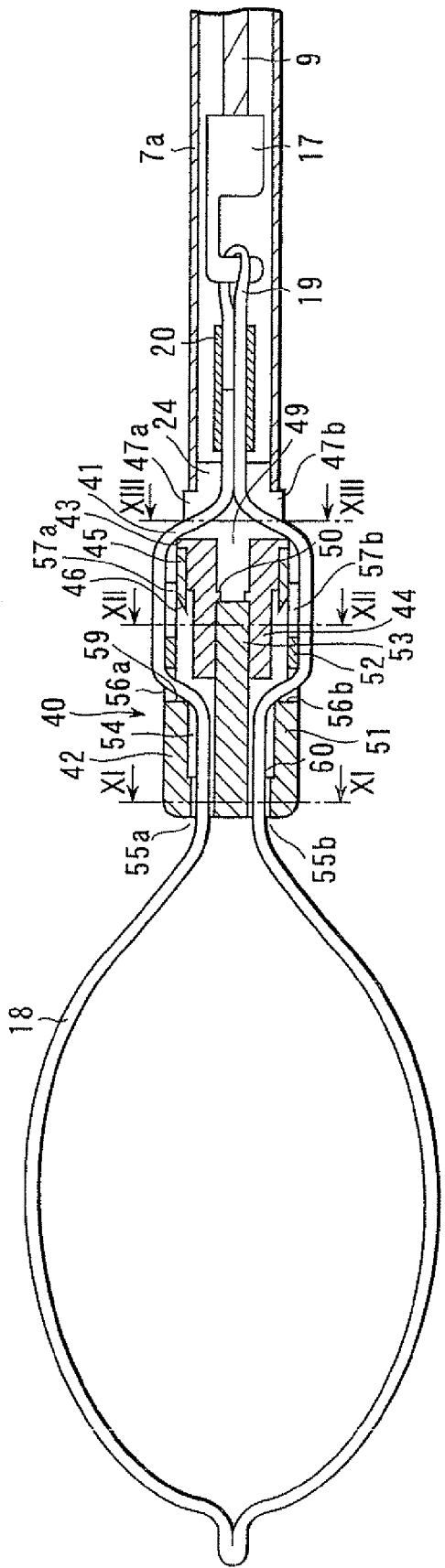
FIG. 9 is a longitudinal side cross section showing a distal end of a medical ligating apparatus according to a fourth embodiment of the present invention.
Figure 10:
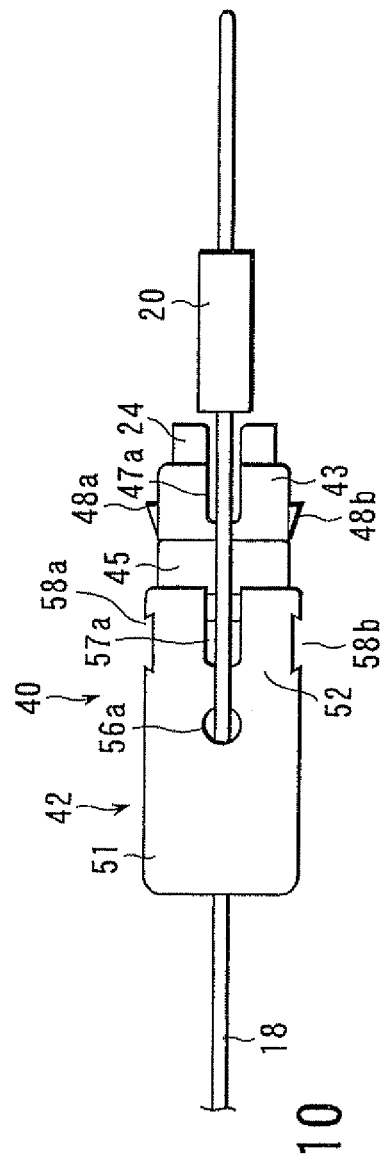
FIG. 10 is a plan view showing a distal end of the medical ligating apparatus according to the fourth embodiment.
Figure 13:
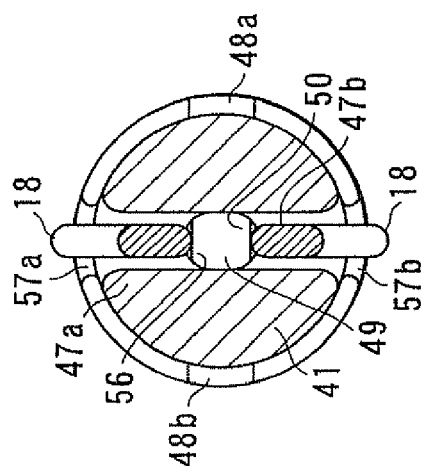
FIG. 13 is a sectional view taken along the line XIII-XIII of FIG. 9.
Figure 12:
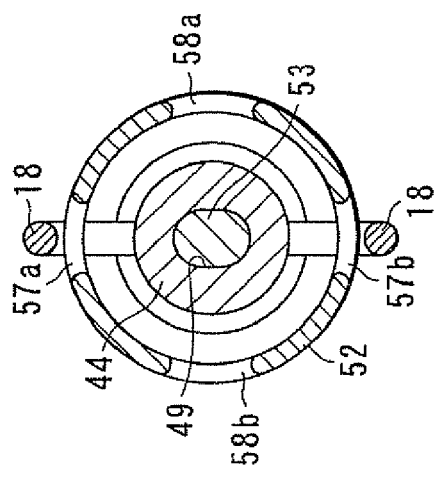
FIG. 12 is a sectional view taken along the line XII-XII of FIG. 9.
Figure 11:
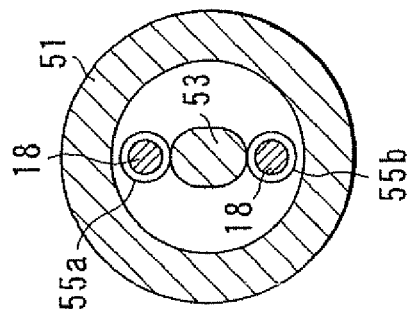
FIG. 11 is a sectional view taken along the line XI-XI of FIG. 9.
Figure 14:
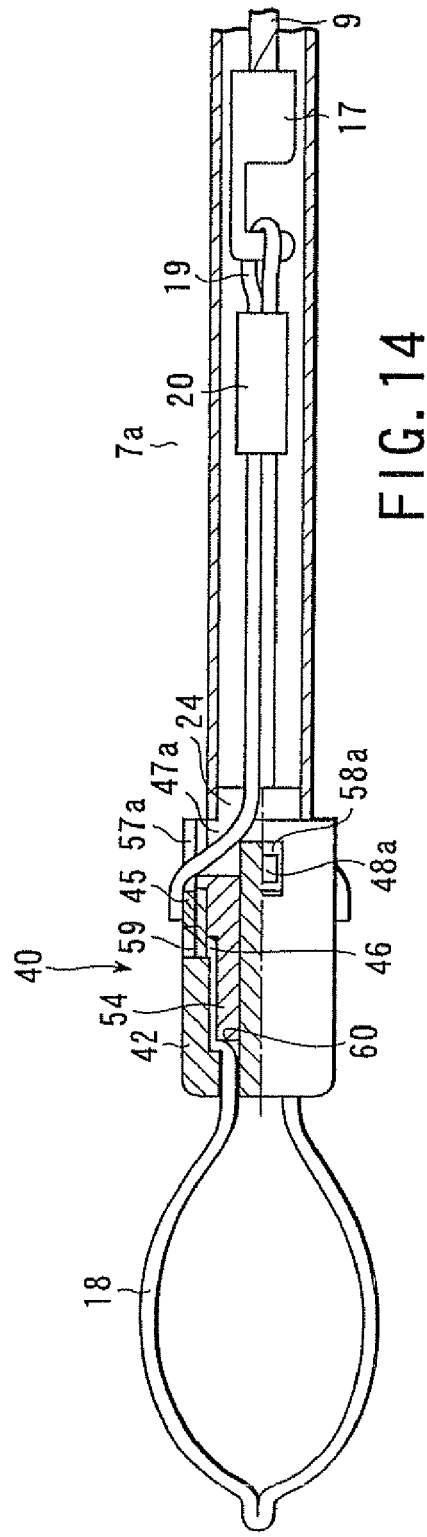
FIG. 14 is a longitudinal side cross section showing a distal end of the medical ligating apparatus in a state in which the ligating wire of the fourth embodiment is cut.

FIG. 9 to FIG. 14 show a fourth embodiment of the present invention. Like elements in the first embodiment are designated by like reference numerals. A duplicate description is omitted here. FIG. 9 is a longitudinal side cross section showing a distal end side of a medical ligating apparatus. FIG. 10 is a plan view showing the same. FIG. 11 is a cross section taken along the line XI-XI. FIG. 12 is a sectional view taken along the line XII-XII. FIG. 13 is a sectional view taken along the like XIII-XIII. FIG. 14 is a longitudinal side cross section showing a distal end side of a medical ligating apparatus in a state in which a ligating wire is cut.

A fixing member 40 is provided at the proximal end side of the ligating wire 18. This fixing member 40 is preferably made of a plastic such as polypropylene, ABS, polyacetal, polycarbonate, or alternatively, a comparatively rigid material with excellent fluidity such as a liquid crystal polymer or polyphthal amide. This member may be made of a metal such as stainless or aluminum, is about 1 mm to 3 mm in external diameter, and is about 5 mm to 10 mm in length.

The fixing member 40 is composed of a first member 41 and a second member 42. The first member 41 is formed in a cylindrical shape. A large diameter section 43 is provided at a proximal end of the first member, and a press-in section 44 consisting of a short diameter section is provided at a distal end thereof. An annular cutting member 45 is engagingly fitted to the outer periphery at the distal end side of the large diameter section 43 while its cutting blade 46 is oriented to the distal end side. Wire guides 47a, 47b are provided at the top and bottom portions of the outer periphery of the proximal end side of the large diameter section 43. Further, at the outer periphery of the distal end side of the large diameter section 43, engagement claws 48a, 48b are provided at the right and left parts which are biased by 90 degrees in a peripheral direction relative to the wire guides 47a, 47b. In addition, at a coaxial section of the first member 41, an internal cavity 49 is provided in an axial direction. A protrusion 50 is provided at the substantially intermediate section in the axial direction of this internal cavity 49. The height of this protrusion 50 is between 0.1 mm to 0.3 mm.

In the second member 42, a columnar section 51 is provided at its distal end, and a cylindrical section 52 is provided integrally with the columnar section 51 at its proximal end. At the center of the columnar section 51, an insert shaft 53 to be inserted into the internal cavity 49 of the first member 41 is protruded through the inner of the cylindrical section 52. Further, a fixing internal cavity 54 into which a press-in section 44 of the first member 41 is to be pressed is provided at the columnar section 51 so as to surround the insert shaft 53. The length of the fixing internal cavity 54 is between 1 mm to 3 mm.

In addition, distal end holes 55a, 55b into the ligating wires 18 are inserted one by one are provided at the distal face of the second member 42. Side holes 56a, 56b are provided at the top and bottom parts at the outer periphery of the cylindrical section 52 of the second member 42. Slits 57a, 57b are provided in the neighborhood of these holes. Further, at the cylindrical section 52, engagement holes 58a, 58b to be engaged with the engagement claws 48a, 48b of the first member 41 are provided at the right and left parts which are biased by 90 degrees in a peripheral direction relative to the slits 57a, 57b. In addition, an abutment face 59 of the cutting blade 46 is provided on an end face at the proximal end side of the columnar section 51 of the second member 42, and an abutment section 60, on which the press-in section 44 abuts, is provided in the vicinity of the distal end of the fixing internal cavity 54. A single-side clearance between an internal diameter of the fixing internal cavity 54 and an external diameter of the press-in section 44 is defined so as to be smaller than an external diameter of the ligating wire 18.

The insert shaft 53 of the second member 42 is inserted into the internal cavity 49 of the first member 41, and a distal face of the insert shaft 53 abuts against the protrusion 50, whereby the insertion depth is restricted. Therefore, the cylindrical section 52 of the second member 42 is engaged with the outer of the cutting member 45 so as to cover the cutting blade 46.

The ligating wire 18 is inserted from the distal end holes 55a, 55b into the inner of the second member 42, and is led out to the outer through the side holes 56a, 56b. Further, the ligating wire 18 is guided by the slits 57a, 57b and wire guides 47a, 47b, and is led to the proximal end side of the fixing member 40. Connection between the fold section 19 of the ligating wire 18 and both of the ends via the connecting pipe 20 is similar to that in the first embodiment.

Next, an operation of a fourth embodiment will be described.

First, the manipulating wire 9 is advanced, whereby the engagement member 17 is protruded from a distal opening of the sheath 7a. In this state, the fold section 19 at the proximal end of the ligating wire 18 is hooked on a hook section of the engagement member 17. When the manipulating wire 9 is retracted, thereby introducing the engagement member 17 into the inner of the sheath 7a, the converging section 24 of the fixing member 40 is supported after being inserted into the distal opening of the sheath 7a. In this state, the sheath 7a including the ligating wire 18 is inserted through the endoscope channel, and is inserted into the body cavity. Then, the distal end of the sheath 7a is guided to a target site in the body cavity. While the lesion 28 such as polyp is observed by means of the endoscope, when the sheath 7a is advanced, the ligating wire 18 is protruded from the distal opening of the channel. Then, the loop section of the ligating wire 18 is elastically restored, and is increased in diameter, as shown in FIG. 9.

Next, while the lesion 28 is observed by means of the endoscope, after the loop section of the ligating wire 18 is hooked on the root of the lesion 28, when the manipulating wire 9 is retracted, the proximal end of the ligating wire 18 is introduced into the inner of the sheath 7a via the engagement member 17. Then, the ligating wire 18 is reduced in diameter, and the lesion 28 is tightly bound.

When the manipulating wire 9 is further retracted, the distal face of the second member 42 of the fixing member 40 abuts against the lesion 28, and the lesion 28 serves as a stopper. Thus, the first member 41 is relatively advanced, and the second member 42 is retracted. Therefore, the insert shaft 53 of the second member 42 breaks the protrusion 50, and is inserted into the internal cavity 49 of the first member 41.

In addition, the press-in section 44 of the first member 41 is advanced in the direction of the fixing internal cavity 54 of the second member 42. Thus, the intermediate section of the ligating wire 18 is fixed to be pinched between an internal face of the fixing internal cavity 54 and an external face of the press-in section 44. Further, when the press-in section 44 of the first member 41 is advanced in the direction of the fixing internal cavity 54 of the second member 42, the cutting blade 46 of the cutting member 45 provided at the first member 41 abuts against an abutment face 59 of the second member 42. Therefore, when the intermediate section of the ligating wire 18 is cut, and a cut end is pinched and fixed between the internal face of the fixing internal cavity 54 and the external face of the press-in section 44.

In addition, when the distal end of the press-in section 44 abuts against an abutment section 60, the engagement claws 48a, 48b of the first member 41 are engaged with the engagement holes 58a, 58b, and the first member 41 is engaged with the second member 42.

The sheath 7a and the fixing member 40 are separated from each other by disconnection of the ligating wire 18, and the ligating device 2 and manipulating device 3 are completely separated from each other. When the sheath 7a is drawn from the endoscope channel, only the ligating wire 18 held in a tightly bound state by means of the fixing member 40 is retained in the body, and a surgical operation for tightly binding the lesion 28 completes.

In this way, according to the medical ligating apparatus 1, a manipulation for cutting and separating the ligating wires 18 at the same time when the lesion 28 is tightly bound by the ligating wire 18 can be carried out in series. Therefore, unlike the prior art, there is no need to replace the ligating apparatus with the scissors in the endoscope channel, and a surgical operation time can be reduced. Moreover, the cut end of the ligating wire 18 is housed at the inner of the fixing member 40, and thus, interference with another treatment device or an endoscope can be prevented more effectively. In addition, the cutting member 45 is provided at the medical ligating device 2 itself. Thus, a new cutting blade is always used without repeated use of the cutting blade 46. As a result, the ligating wire 18 can be cut reliably.

The cutting member 45 is provided at the inner of the fixing member 40, whereby a protrusion is eliminated. Thus, the outer sheath becomes unnecessary, and the wire can be directly inserted through the endoscope channel. The outer sheath becomes unnecessary, whereby the insert section 4 of the medical ligating apparatus 1 can be reduced in diameter, and the wire can be inserted through a channel with its small internal diameter.

Figure 16:
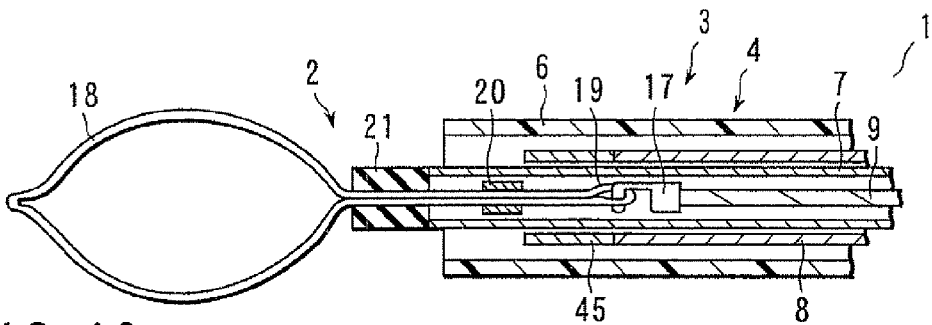
FIG. 16 is a longitudinal side cross section showing a distal end of a medical ligating apparatus according to a fifth embodiment of the present invention.
Figure 17:
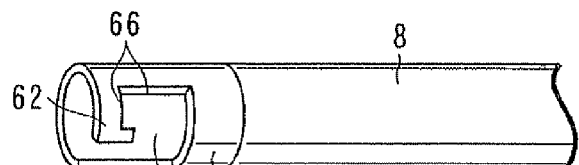
FIG. 17 is an external view showing a distal end of a cutting sheath according to the fifth embodiment.

FIG. 16 to FIG. 18 show a fifth embodiment of the present invention. FIG. 16 is a longitudinal side cross section showing a distal end of the apparatus. FIG. 17 is an external view showing a distal end of a cutting sheath. FIG. 18 is a perspective view showing a state during ligation. Only differences from the first to third embodiments will be described here.

As shown in FIG. 16, an external diameter of the stopper 21 is substantially equal to that of the inner sheath 7, and a distal face of the inner sheath 7 can abut against a proximal face of the stopper 21. A cutting sheath 8 is formed of a metallic meshed plastic (for example, polyethylene, PTFE, nylon or the like), or alternatively, a metallic multi-striped coil, and is excellent in rotation tracking properties.

As shown in FIG. 17, a cutting member 65 is connected at a distal end of the cutting sheath 8. The cutting member 65 has a cutout 61. A cutting blade 66 is provided at the distal edge and side face edge of the cutout 61. A claw section 62 is provided at the distal end side of the cutout 61.

Next, an operation of a fifth embodiment of the invention will be described.

After the loop section of the ligating wire 18 has been hooked on the lesion 28, the slider 12 is pulled toward the proximal side, and the lesion 28 is ligated. Then, the slider 12 is slightly pushed and advanced to the distal end side, and a portion of the ligating wire 18 at the proximal end side of the stopper 21 is exposed to the distal end side of the inner sheath 7, as shown in FIG. 18A.

Next the cutting manipulating section 13 is manipulated, whereby the cutting sheath 8 is advanced to be protruded to the distal end side more than the inner sheath 7. In this state, by using a bending manipulation of the endoscope or the like, the ligating wire 18 exposed as shown in FIG. 18B is hooked on a claw section 62.

Figures 18A, 18B:
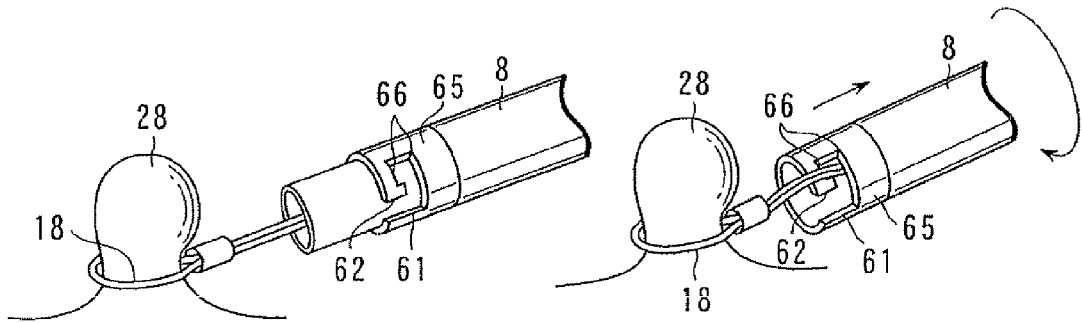
FIG. 18A and FIG. 18B are perspective views showing a state during ligation according to the fifth embodiment.

Then, the cutting manipulating section 13 is pulled to the proximal side or is rotated in the direction shown in FIG. 18B, whereby a cutting blade 66 provided at a cutting member 65 cuts the ligating wire 18 at the proximal end side of the stopper 21.

According to the present embodiment, unlike the first to third embodiments, there is no need to provide a receiving member at the medical ligating device 2, and the number of parts is reduced. Thus the manufacturing cost can be reduced. In addition, the ligating wire 18 does not pass through the distal end holes 25*a*, 25*b* and proximal end holes 26*a*, 26*b* of the receiving member in a bent state, and extends straight between a proximal end of the stopper 21 and the engagement member 17. This makes it possible to push and advance the stopper 21 to the distal end side with a gentle force when the lesion 28 is ligated.

Figure 19:
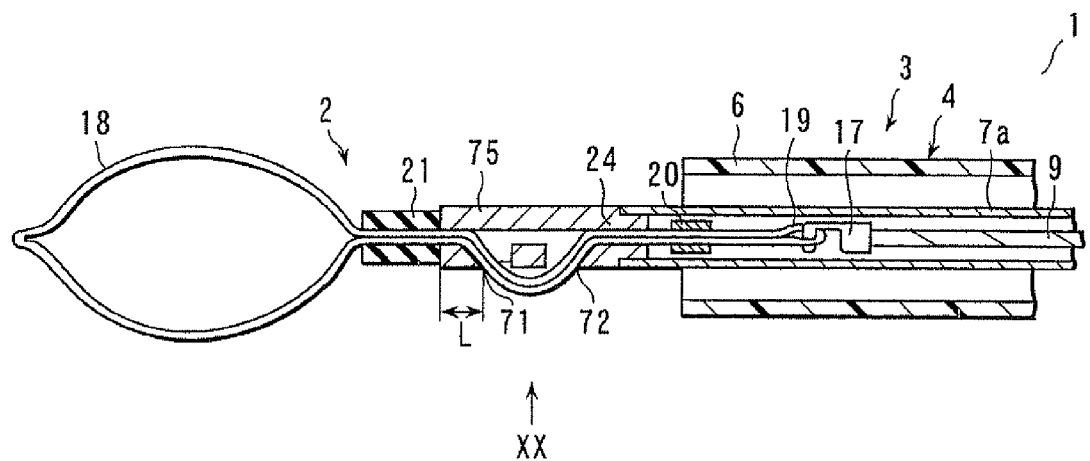
FIG. 19 is a longitudinal side cross section showing a distal end of a medical ligating apparatus according to a sixth embodiment of the present invention.
Figure 20:
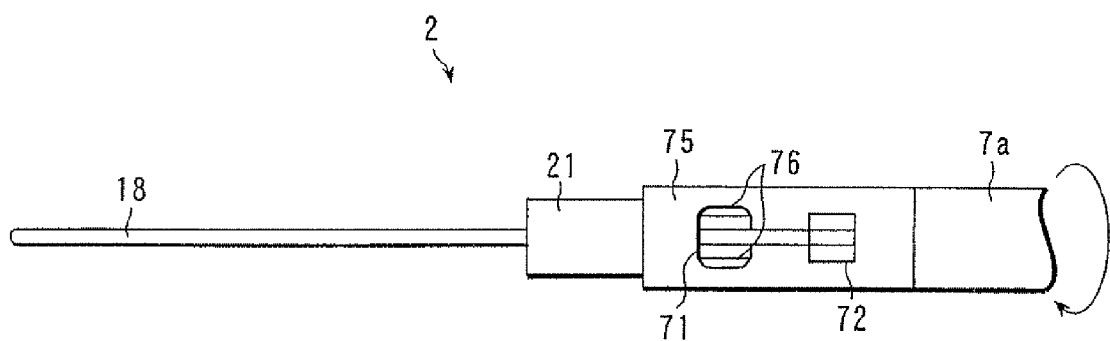
FIG. 20 is an external view showing the apparatus in a direction indicated by the arrow XX in FIG. 19 according to the sixth embodiment.

FIG. 19 and FIG. 20 show a sixth embodiment of the present invention FIG. 19 is a longitudinal side cross section showing a distal end of the apparatus. FIG. 20 is an external view of the apparatus in the direction indicated by the arrow XX in FIG. 19. Only differences from the first to third embodiments will be described here.

An annular cutting member 75 is provided at the proximal end side of the stopper 21. The cutting member 75 is formed of a metal member such as stainless. A converging section 24 is provided at the proximal end side of the cutting member 75, and is designed to enable engagement with a distal internal cavity of the sheath 7*a*. An external diameter of the converging section 24 is slightly larger than the distal internal diameter of the sheath 7*a*. This external diameter is defined in a dimension such that the cutting member 75, when engaged with the distal internal cavity of the sheath 7*a*, does not slip off easily nor rotate relative to the sheath 7*a*.

In addition, the sheath 7*a* is formed of a metallic meshed plastic (for example, polyethylene, PTFE, or nylon and the like), or alternatively, a metallic multi-stripe coil, and is excellent in rotation tracking properties.

A distal end hole 71 and proximal end hole 72 through which two ligating wires 18 can be inserted are provided on a side face of the cutting member 75. These holes communicate with an internal cavity of the cutting member 75. After the ligating wire 18 has passed through the inner of the stopper 21, the ligating wire enters a distal opening of the cutting member 75. Then, the ligating wire 18 is exposed to the outer through the distal end hole 71. Further, the ligating wire 18 extends to the engagement member 17 through the proximal end hole 72, an internal cavity of the cutting member 75, and an internal cavity of the sheath 7*a*.

It is desirable that a distance L between the distal end of the cutting member 75 and the distal end hole 71 be short. The distance L is set to about 2 mm to 5 mm. In addition, a cutting blade 76 is provided at both edges of the distal end hole 71.

Next, an operation of a sixth embodiment will be described.

After the lesion 28 has been ligated at the loop section of the legating wire 18, the proximal end side of the sheath 7*a* is rotated. The cutting member 75 and the distal end of the sheath 7*a* are engaged with each other so as not to easily rotate therebetween. Thus, the cutting member 75 rotates in unison with the sheath 7*a*.

The distal end side of the ligating wire 18 is fixed to be ligated around the lesion 28. Thus, when the cutting member 75 rotates, the cutting blade 76 abuts against a portion of the ligating wire 18 which is passing through the distal end hole 71, and cuts the portion of the wire. When the manipulating device 3 is removed from the endoscope, the cutting member 75 is taken out of the body while it is fixed to the distal end of the sheath 7*a*.

The cutting blade 76 may be provided at a distal edge of the distal end hole 71. In this case, the sheath 7*a* is pulled to the proximal side, whereby the ligating wire 18 is cut by the cutting blade 76. In this case, the sheath 7*a* and converging section 24 must be set so as not to be disengaged from each other in the range of a force required to cut the ligating wire 18.

According to the present embodiment, the cutting member 75 is provided in place of the receiving members according to the first to third embodiments. As a result, the cutting sheath 8 becomes unnecessary, the number of parts is reduced, and the manufacturing cost can be reduced. In addition, unlike the first to third embodiments, the medical ligating device is not retained in the body in such a state that another member remains at the proximal end side of the fixing member. Thus, interference with another treatment device or an endoscope can be prevented more efficiently immediately after the ligating device has been retained.

As has been described above, a manipulation for tightly binding a lesion by a ligating member and a manipulation for cutting the ligating member can be carried out in series. In addition, there is no need to replace the ligating apparatus with the scissors in the endoscope channel, and a surgical operation time can be reduced. Moreover, the ligating member can be cut at a portion close to the fixing member. Thus, the cut end of the ligating member does not remain in the body cavity while it is extended, and interference with another treatment device or an endoscope can be prevented. In addition, the cutting blade extends in the longitudinal direction of the manipulating device. Thus, the manipulating device can be reduced in diameter. Further, means for cutting the ligating member is formed with a simple structure. Thus, the manufacturing cost can be reduced. Note that the ligating device is not limited to a loop-shaped one.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical ligating apparatus comprising:
a manipulating device including a flexible outer sheath having a central axis, an elongate member extending along the central axis in the flexible outer sheath, and a proximal manipulation section provided on a proximal side of the outer sheath;
a medical ligating device configured to be removably attached to a distal end side of the manipulating device, the medical ligating device including a flexible wire which has a folded loop section, two opposite intermediate sections respectively extended in a proximal direction from opposite ends of the folded loop section along the central axis of the flexible outer sheath, and a proximal end portion extended from the intermediate sections and configured to be connected to a distal end of the elongate member, a hollow fixing member through which said two opposite end side sections are extended so that the hollow fixing member and said two opposite end side sections are relatively movably along the central axis, and a hollow receiving member through which the intermediate sections are extended in the proximal direction, the hollow receiving member including at least one abutment face directed in the proximal direction, wherein the hollow fixing member is positioned between the hollow receiving member and the folded loop section of the flexible wire; and a cutting member configured to be moveable along the central axis in the flexible outer sheath, the cutting member including at least one cutting blade directed in a distal direction, wherein the proximal manipulation section includes a first manipulating member connected to a proximal end of the elongate member to move the flexible wire along the central axis relative to the flexible outer sheath, and a second manipulating member configured to move the cutting member along the central axis relative to the hollow receiving member, wherein living tissues are to be ligated in the folded loop section of the flexible wire and said two opposite intermediate sections are pulled in the proximal direction to apply a tensile stress to at least parts of the opposite intermediate sections facing the abutment face, by moving the flexible wire relative to the hollow receiving member in the proximal direction through the first manipulating member in a state that the medical ligating device is attached to the distal end side of the manipulating device, and then the cutting member is moved in the distal direction by the second manipulating member so that the cutting blade pushes said parts of the opposite intermediate sections applied with the tensile stress toward the abutment face and abuts the abutment face, thereby cutting off said parts.

2. The medial ligating apparatus according to claim 1, wherein the elongate member includes an engaging member provided at a distal end, and the proximal end portion of the flexible wire includes looped wire portion extended from the opposite intermediate sections which is configured to engage with the engaging member.

3. The medical ligating apparatus according to claim 1, wherein the receiving member is removed from the manipulating device in a state that living tissues are ligated in the folded loop section of the flexible wire and fixed by the fixing member, and the opposite end side sections are cut off so that the medical ligating device is kept in a body including the living tissues.

4. The medical ligating apparatus according to claim 1, wherein the hollow receiving member includes a cylindrical body having a central through hole extending along the central axis of the flexible outer sheath, one pair of first radial through holes and one pair of second through radial holes which are radially extended to an outer peripheral surface from the central through holes, and an annular projection extended from the outer peripheral surface between the first radial through holes and the second radial through holes, the annular projection defining the abutment face at a proximal end surface, and wherein the opposite intermediate sections pass through the central through holes with intermediate parts passing the first radial through holes, on a peripheral surface of the annular projection and then the second radial through holes.

5. The medical ligating apparatus according to claim 4, wherein each pair of the first and second radial through holes are aligned with each other in a radial direction, so that portions of the opposite intermediate sections facing the abutment face are separated with each other by substantially 180 degrees.

6. The medical ligating apparatus according to claim 5, wherein the cutting member includes a cylindrical body and the cutting blade is a circular shape provided on a distal end of the cylindrical body.

7. The medical ligating apparatus according to claim 6, wherein the manipulating device includes an inner sheath provided in the cylindrical body of the cutting member to be coaxial therewith, so that the inner sheath guides the cutting member upon a movement of the cutting member.

8. The medical ligating apparatus to claim 7, wherein the cylindrical body of the hollow receiving member is detachably attached to a distal end of the inner sheath at a proximate end.

9. The medical ligating apparatus according to claim 8, wherein the flexible outer sheath is movable along the central axis relative to the inner sheath so that the folded loop section of the flexible wire is received into the flexible outer sheath.

10. A medical ligating apparatus comprising:

a manipulating device including flexible outer sheath having a central axis, an elongate member extending along the central axis in the flexible outer sheath, and a proximal manipulation section provided on a proximal side of the outer sheath;

a medical ligating device configured to be removably attached to a distal end side of the manipulating device, the medical ligating device including a flexible wire which has a folded loop section, two opposite intermediate section respectively extended in a proximal direction from opposite ends of the folded loop section along the central axis of the flexible outer sheath, and a proximal end portion extended from the intermediate sections and configured to be connected to a distal end of the elongate member, a hollow fixing member through which said two opposite end side sections are extended so that the hollow fixing member and said two opposite end side sections are relatively movably along the central axis, and a hollow receiving member through which the intermediate sections are extended in the proximal direction, the hollow receiving member including at least one abutment face, wherein the hollow fixing member is positioned between the hollow receiving member and the folded loop section of the flexible wire; and a cutting member configured to be movable along the central axis in the flexible outer sheath, the cutting member including at least one cutting blade directed in a direction of said at least one abutment face, wherein the proximal manipulation section includes a first manipulating member connected to a proximal end of the elongate member to move the flexible wire along the central axis relative to the flexible outer sheath, and a second manipulating member configured to move the cutting member along the central axis relative to the hollow receiving member, wherein living tissues are to be ligated in the folded loop section of the flexible wire and said two opposite intermediate sections are pulled in the proximal direction to apply a tensile stress to at least parts of the opposite intermediate sections facing the abutment face, by moving the flexible wire relative to the hollow receiving member in the proximal direction through the first manipulating member in a state that the medical ligating device is attached to the distal end side of the manipulating device, and then the cutting member is moved toward the abutment face by the second manipulating member, so that the cutting blade pushes said parts of the opposite intermediate sections, applied with the tensile stress toward the abutment face and abuts the abutment face, thereby cutting off said parts at the substantially same time.

* * * * *